US007525009B2

(12) United States Patent
Blann et al.

(10) Patent No.: US 7,525,009 B2
(45) Date of Patent: Apr. 28, 2009

(54) TRIMERISATION OF OLEFINS

(75) Inventors: Kevin Blann, Alberton (ZA); Annette Bollmann, Henley-on-Klip (ZA); John Thomas Dixon, Vanderbijlpark (ZA); Arno Neveling, Sasolburg (ZA); David Hedley Morgan, Sasolburg (ZA); Hulisani Maumela, Johannesburg (ZA); Esna Killian, Vanderbijlpark (ZA); Fiona Millicent Hess, Sasolburg (ZA); Stefanus Otto, Sasolburg (ZA); Matthew James Overett, Johannesburg (ZA)

(73) Assignee: Sasol Technology (Pty) Limited, Johannesburg (ZA)

( * ) Notice: Subject to any disclaimer, the term of this patent is extended or adjusted under 35 U.S.C. 154(b) by 73 days.

(21) Appl. No.: 10/539,137

(22) PCT Filed: Dec. 19, 2003

(86) PCT No.: PCT/ZA03/00185

§ 371 (c)(1),
(2), (4) Date: Apr. 7, 2006

(87) PCT Pub. No.: WO2004/056477

PCT Pub. Date: Jul. 8, 2004

(65) Prior Publication Data

US 2006/0211903 A1 Sep. 21, 2006

Related U.S. Application Data

(60) Provisional application No. 60/435,405, filed on Dec. 20, 2002, provisional application No. 60/478,379, filed on Jun. 13, 2003, provisional application No. 60/509,309, filed on Oct. 6, 2003.

(30) Foreign Application Priority Data

| | | |
|---|---|---|
| Dec. 20, 2002 | (ZA) | 2002/10339 |
| Jan. 13, 2003 | (ZA) | 2003/4632 |
| Oct. 6, 2003 | (ZA) | 2003/7774 |

(51) Int. Cl.

| | |
|---|---|
| *C07C 2/08* | (2006.01) |
| *C07C 2/32* | (2006.01) |
| *B01J 2/08* | (2006.01) |
| *B01J 31/18* | (2006.01) |
| *B01J 31/22* | (2006.01) |
| *B01J 31/24* | (2006.01) |

(52) U.S. Cl. ...................... 585/527; 585/513; 585/514; 502/103; 502/121; 502/124

(58) Field of Classification Search ................ 585/527, 585/513, 514, 516; 502/102, 121, 124, 125, 502/103

See application file for complete search history.

(56) References Cited

U.S. PATENT DOCUMENTS

| | | | | |
|---|---|---|---|---|
| 3,635,937 | A | 1/1972 | Bauer et al. | |
| 3,676,523 | A | 7/1972 | Mason | |
| 3,906,053 | A | 9/1975 | Lanier | |
| 4,668,838 | A * | 5/1987 | Briggs | 585/513 |
| 5,786,431 | A | 7/1998 | Reagen et al. | |
| 5,856,610 | A | 1/1999 | Tamura et al. | |
| 6,184,428 | B1 | 2/2001 | Zahoor et al. | |
| 7,022,788 | B2 * | 4/2006 | Wass | 526/172 |
| 2005/0119516 | A1 * | 6/2005 | Dixon et al. | 585/665 |

FOREIGN PATENT DOCUMENTS

| | | | |
|---|---|---|---|
| DE | 1 443 927 | | 10/1962 |
| WO | WO 02/04119 | A1 | 1/2002 |
| WO | WO 03/053890 | A1 | 7/2003 |
| WO | WO 03/053891 | A1 | 7/2003 |

* cited by examiner

*Primary Examiner*—Caixia Lu
(74) *Attorney, Agent, or Firm*—Finnegan, Henderson, Farabow, Garrett, & Dunner, L.L.P.

(57) ABSTRACT

The invention describes a process for trimerisation olefins, which process includes the step of contacting an olefinic feedstream with a catalyst system which includes a transition metal compound and a heteroatomic ligand and wherein the trimer is an olefin and wherein the heteroatomic ligand is described by the following general formula $(R)_nA\text{-}B\text{-}C(R)_m$.

28 Claims, No Drawings

TRIMERISATION OF OLEFINS

CROSS REFERENCE TO RELATED APPLICATIONS

This application is a National Phase application based on PCT/ZA2003/000185, filed on Dec. 19, 2003, the contents of which are incorporated herein by reference and claims the priority of South African Application No. 2002/10339, filed on Dec. 20, 2002, South African Application No. 2003/4632, filed on Jun. 13, 2003, South African Application No. 2003/7774, filed on Oct. 6, 2003, and claims the benefit of U.S. Provisional Application No. 60/435,405, filed on Dec. 20, 2002, U.S. Provisional Application No. 60/478,379, filed on Jun. 13, 2003, and U.S. Provisional Application No. 60/509,309, filed on Oct. 6, 2003, the contents of each of which are incorporated herein by reference.

FIELD OF THE INVENTION

This invention relates to an olefin trimerisation process, a catalyst system for trimerisation of olefins and the identification and use of ligands for a catalyst system for trimerisation of olefins.

BACKGROUND OF THE INVENTION

1-Hexene is an important commercial product. In addition to its use as a specific chemical, it is also extensively used in polymerisation processes either as a monomer or co-monomer. This invention defines a catalyst system that facilitates the production of 1-hexene from ethylene in high selectivity, while avoiding the co-production of significant quantities of other higher oligomers and polyethylene.

In this regard, it is known from prior art (U.S. Pat. No. 6,184,428) that a nickel catalyst comprising a chelating ligand, preferably 2-diphenyl phosphino benzoic acid (DPPBA), a nickel precursor, preferably $NiCl_2.6H_2O$, and a catalyst activator, preferably sodium tetraphenylborate, catalyses the oligomerisation of ethylene to yield a mixture of linear olefins containing 1-hexene. The selectivity towards the linear $C_6$ $\alpha$-olefin is claimed to be 33%. Similarly the Shell Higher Olefins Process (SHOP process, U.S. Pat. Nos. 3,676,523 and 3,635,937) using a similar catalyst system is reported to yield 11 mass % 1-hexene in its product mixture (Chem Systems PERP reports 90-1, 93-6 and 94/95S12).

Ziegler-type technologies based on trialkylaluminium catalysts, independently developed by Gulf Oil Chemicals Company (Chevron, e.g. DE patent 1,443,927) and Ethyl Corporation (BP/Amoco, e.g. U.S. Pat. No. 3,906,053), are also commercially used to oligomerise ethylene to mixtures of olefins that reportedly contain 14-25 mass % 1-hexene (Chem Systems PERP reports 90-1, 93-6, and 94/95S12).

The selective trimerisation of ethylene to 1-hexene via transition metal catalysis has been extensively studied and patented. Some of these trimerisation catalysts are capable of trimerising longer chain olefins. This is an important feature, since the trimeric products derived from longer chain olefins could be utilised as synthetic lubricants (e.g. polyalphaolefins/PAOs), as well as in various other applications such as components of drilling muds and as feedstock to prepare detergents and plasticisers. Most of the known catalysts for selective ethylene trimerisation are chromium-based. Recently, chromium-based trimerisation catalyst systems, containing heteroatomic ligands with both phosphorus and nitrogen heteroatoms (WO 03/053891) as well as sulphur and nitrogen heteroatoms (WO 03/053890), have been developed by the applicant. These ligands include a spacer of at least one carbon atom between the heteroatoms to allow true tridentate coordination with the chromium. Tridentate coordination complexes are generally believed to be more selective towards 1-hexene than bidentate complexes. An example of such a heteroatomic ligand for ethylene trimerisation is bis-(2-diethylphosphino-ethyl)-amine. Although the catalyst system containing this ligand is extremely selective towards 1-hexene (with overall 1-hexene selectivity exceeding 96 mass %), it exhibits only moderate catalyst activities.

Another example of such a heteroatomic ligand with both phosphorus and nitrogen heteroatoms for ethylene trimerisation is (o-methoxyphenyl)$_2$PN(Me)P(o-methoxyphenyl)$_2$ as described in WO 02/04119. This patent application discloses the use of ligands described by the following general formula: $(R^1)(R^2)X—Y—X(R^3)(R^4)$ wherein X is phosphorus, arsenic or antimony; Y is a linking group such as $—N(R^5)—$ and $R^1$, $R^2$, $R^3$ and $R^4$ are each independently hydrocarbyl, substituted hydrocarbyl, heterohydrocarbyl or substituted heterohydrocarbyl groups, at least one of which has a polar substituent which is not a phosphane, arsane or stibane group. The ethylene trimerisation catalyst system containing (o-methoxyphenyl)$_2$PN(Me)P(o-methoxyphenyl)$_2$ is somewhat less selective (claimed selectivities towards 1-hexene range between 75 and 91.5 mass %) than the system described in WO 03/053891, but it is more active. Thus, based on the above description, an essential attribute of the ligands disclosed in this patent application, is that at least one of the $R^1$, $R^2$, $R^3$ and $R^4$ groups must have a polar, or electron donating, substituent. Open literature shows that the use of (o-ethylphenyl)$_2$PN(Me)P(o-ethylphenyl)$_2$, a compound without any such polar substituents on at least one of $R^1$, $R^2$, $R^3$ and $R^4$, as a ligand under catalytic conditions resulted in no catalytic activity towards 1-hexene (Anthea Carter et al., *Chem. Commun.,* 2002, 858-859). The coordinating phosphorus heteroatoms in the above-mentioned ligand are spaced apart by one nitrogen atom. It is believed that the nitrogen atom does not coordinate with the chromium (at least in the absence of an activator) and that without any further electron donating atoms on the ligand, it is a bidentate system. It is further believed that any polar, or electron donating substituents especially in the ortho-position of the phenyl groups ($R^1$, $R^2$, $R^3$ and $R^4$) facilitate the formation of a tridentate system. This feature is reiterated in *Chem. Commun.,* 2002, 858-859 by stating; "This has led us to hypothesise that the potential for ortho-methoxy groups to act as pendent donors and increase the coordinative saturation of the chromium centre is an important factor."

The applicant has now shown that, contrary to the findings of Carter et al., excellent ethylene trimerisation activities and selectivities are indeed possible using inexpensive PNP ligands containing non-polar substituents on the ortho positions of the phenyl rings attached to the phosphorus. Higher overall selectivities are in fact achievable when using these ligand systems compared to ligands in which the ortho position has a polar substituent as was reported by Carter et al.

SUMMARY OF THE INVENTION

This invention relates to a process for selectively producing trimeric products such as 1-hexene from olefins by using a transition metal catalyst system containing a heteroatomic ligand.

According to a first aspect of the invention there is provided a process for the trimerisation of olefins, which process includes the step of contacting an olefinic feed stream with a catalyst system which includes a heteroatomic ligand and a transition metal compound.

The term trimerisation means the catalytic reaction of a single olefinic monomer or a mixture of olefinic monomers giving products enriched in trimers derived from those olefinic monomers. The product stream may consist of linear and/or branched olefins The feedstream includes an olefin or a mixture of olefins to be trimerised and can be introduced into the process according to the invention in a continuous or batch fashion.

The product stream includes a trimer, which trimer is produced according to the invention in a continuous or batch fashion.

The process may include a process for trimerisation of α-olefins wherein α-olefins include all hydrocarbon compounds with terminal double bonds. This definition includes ethylene, propylene, 1-butene, isobutylene, 1-pentene, 1-hexene, 1-octene and the like.

The process may include a process for trimerisation of α-olefins to yield trimeric α-olefin products selectively.

The ethylene may be contacted with the catalyst system at a pressure of 1 barg, preferably greater than 10 barg, more preferably greater than 30 barg.

By heteroatomic is meant a ligand that contains at least two heteroatoms, which may be the same or different, and may be independently selected from any one of a group which comprises phosphorus, arsenic, antimony, sulphur, nitrogen, oxygen, bismuth and selenium. The heteroatomic ligand may be described by the following general formula $(R)_nA\text{-}B\text{—}C(R)_m$ where A and C are independently selected from a group which comprises phosphorus, arsenic, antimony, oxygen, bismuth, sulphur, selenium, and nitrogen, and B is a linking group between A and C, and R is independently selected from any homo or hetero hydrocarbyl group and n and m are determined by the respective valence and oxidation state of A and C.

More specifically the ligand may be described by the following general formula: $(R^1)(R^2)A\text{-}B\text{—}C(R^3)(R^4)$, where A and C are independently phosphorus, arsenic, antimony, nitrogen and bismuth and B is a linking group between A and C. A and/or C may be a potential donor site for coordination with the transition metal.

An electron donor is defined as that entity that donates electrons used in chemical, including dative covalent, bond formation.

A and/or C may be independently oxidised by S, Se, N or O.

A and C may be independently phosphorus or phosphorus oxidised by S or Se or N or O.

The heteroatomic ligand may be selected from a group of ligands having at least two heteroatoms, wherein each heteroatom contains hydrocarbyl or heterohydrocarbyl groups without any electron donating substituents. The applicant believes that if the catalyst system contains a bidentate heteroatomic coordination complex with substituents on the ortho position of any aromatic group bound to A or C, it would lead to improvements in the selectivity of the catalyst system due to suppression of secondary trimerisation reactions. In addition, the applicant has surprisingly found that in most instances the presence of non-electron donating substituents is beneficial in terms of the overall reaction selectivity towards 1-hexene.

B may be selected from any one of a group comprising: organic linking groups comprising a hydrocarbyl, substituted hydrocarbyl, heterohydrocarbyl and a substituted heterohydrocarbyl group; inorganic linking groups comprising single atom links; ionic linking groups and a group comprising methylene, dimethylmethylene, 1,2-ethane, 1,2-phenylene, 1,2-propane, 1,2-catechol, 1,2-dimethylhydrazine, $\text{—}B(R^5)\text{—}$, $\text{—}Si(R^5)_2\text{—}$, $\text{—}P(R^5)\text{—}$ and $\text{—}N(R^5)\text{—}$ where $R^5$ is hydrogen, a hydrocarbyl or substituted hydrocarbyl, a substituted heteroatom or a halogen. Preferably, B may be $\text{—}N(R^5)\text{—}$ and $R^5$ is a hydrocarbyl or a substituted hydrocarbyl group. $R^5$ may be hydrogen or may be selected from the groups consisting of alkyl, aryl, aryloxy, halogen, nitro, alkoxycarbonyl, carbonyloxy, alkoxy, aminocarbonyl, carbonylamino, dialkylamino, or derivatives thereof, and aryl substituted with any of these substituents.

Preferred $R^5$ groups include alkyl groups such as methyl.

B may exclude $(CH_2)_xY(CH_2)_y$, where Y is $\text{—}P(R^6)\text{—}$, $\text{—}N(R^6)\text{—}$, $\text{—}As(R^6)\text{—}$, $\text{—}Sb(R^6)\text{—}$ or —S— and x and y are individually 1-15 and wherein $R^6$ is hydrogen or a halogen or a nitro group or a hydrocarbyl or a substituted hydrocarbyl group.

B may be selected to be a single atom spacer. A single atom linking spacer is defined as a substituted or non-substituted atom that is bound directly to A and C.

$R^1$, $R^2$, $R^3$ and $R^4$ are each independently hydrocarbyl, substituted hydrocarbyl, heterohydrocarbyl or substituted heterohydrocarbyl groups where any substituents are non-electron donating. The substituents may be non-polar groups. Preferably $R^1$, $R^2$, $R^3$ and $R^4$ may be substituted aromatic or substituted hetero-aromatic groups containing non-electron donating substituents on the atom adjacent to the atom bound to A or C. $R^1$, $R^2$, $R^3$ and $R^4$ may be substituted aromatic or substituted hetero-aromatic groups containing non-polar substituents on the atom adjacent to the atom bound to A or C.

Non-polar is defined by IUPAC as an entity without a permanent electric dipole moment.

Suitable non-polar substituents may be a methyl, ethyl, propyl, propenyl, propynyl, butyl, isopropyl, isobutyl, t-butyl, pentyl, hexyl, cyclopentyl, 2-methylcyclohexyl, cyclohexyl, cylopentadienyl, phenyl, bi-phenyl, naphthyl, tolyl, xylyl, mesityl, ethenyl, and benzyl group, or the like.

Preferably two or more of $R^1$, $R^2$, $R^3$ and $R^4$ may be aromatic or hetero aromatic containing at least one non-electron donating substituent on the atom adjacent to the atom bound to A or C. More preferably $R^1$, $R^2$, $R^3$ and $R^4$ may be aromatic or hetero aromatic containing at least one non-polar substituent on the atom adjacent to the atom bound to A or C.

Suitable examples of $R^1$, $R^2$, $R^3$ and $R^4$ include, but are not limited to, methyl, ethyl, ethylenyl, propyl, propenyl, propynyl, butyl, cyclohexyl, 2-methylcyclohexyl, 2-ethylcyclohexyl, 2-isopropylcyclohexyl, benzyl, phenyl, tolyl, xylyl, o-methylphenyl, o-ethylphenyl, o-isopropylphenyl, o-t-butylphenyl, cumyl, mesityl, biphenyl, naphthyl, anthracenyl, methoxy, ethoxy, phenoxy, tolyloxy, dimethylamino, thiomethyl, thiophenyl, trimethylsilyl, dimethylhydrazyl and the like.

$R^1$, $R^2$, $R^3$ and $R^4$ may be independently aromatic or substituted aromatic groups where the substituent on the atom adjacent to the atom bound to A or C is non-electron donating. $R^1$, $R^2$, $R^3$ and $R^4$ may be independently aromatic or substituted aromatic groups where the substituent on the atom adjacent to the atom bound to A or C is not a polar group.

It is most preferred that all of $R^1$, $R^2$, $R^3$ and $R^4$ may be aromatic or hetero aromatic and each of $R^1$, $R^2$, $R^3$ and $R^4$ should be substituted on at least one of the atoms adjacent to the atom bound to A or C by a non-electron donating group. It is also preferred that $R^1$, $R^2$, $R^3$ and $R^4$ be aromatic or hetero aromatic and each of $R^1$, $R^2$, $R^3$ and $R^4$ be substituted on at least one of the atoms adjacent to the atom bound to A or C by a non-polar group.

Any of the groups $R^1$, $R^2$, $R^3$ and $R^4$ may independently be linked to one or more of each other or to the linking group B to form a cyclic structure together with A and C, A and B or B and C.

The ligand may also contain multiple $(R)_nA$-B-$C(R)_m$ units. Not limiting examples of such ligands include dendrimeric ligands as well as ligands where the individual units are coupled either via one or more of the R groups or via the linking group B. More specific, but not limiting, examples of such ligands may include 1,2-di-(N(P(o-ethylphenyl)$_2$)$_2$)-benzene, 1,4-di-(N(P(o-ethylphenyl)$_2$)$_2$)-benzene, N(CH$_2$CH$_2$N(P(o-ethylphenyl)$_2$)$_2$)$_3$ and 1,4-di-(P(o-ethylphenyl)N(methyl)P(o-ethylphenyl)$_2$)benzene.

The ligands can be prepared using procedures known to one skilled in the art and procedures disclosed in published literature. Examples of these ligands are: (o-ethylphenyl)$_2$PN(methyl)P(o-ethylphenyl)$_2$, (o-isopropylphenyl)$_2$PN(methyl)P(o-isopropylphenyl)$_2$, (o-methylphenyl)$_2$PN(methyl)P(o-methylphenyl)$_2$, (o-ethylphenyl)$_2$PN(methyl)P(o-ethylphenyl)(phenyl), (o-ethylphenyl)$_2$PN(isopropyl)P(o-ethylphenyl)$_2$, (o-isopropyl)$_2$PN(isopropyl)P(o-isopropyl)$_2$, (o-methyl)$_2$PN(isopropyl)P(o-methyl)$_2$, (o-t-butylphenyl)$_2$PN(methyl)P(o-t-butylphenyl)$_2$, (o-t-butylphenyl)$_2$PN(isopropyl)P(o-t-butylphenyl)$_2$, (o-ethylphenyl)$_2$PN(pentyl)P(o-ethylphenyl)$_2$, (o-ethylphenyl)$_2$PN(phenyl)P(o-ethylphenyl)$_2$, (o-ethylphenyl)$_2$PN(p-methoxyphenyl)P(o-ethylphenyl)$_2$, (o-ethylphenyl)$_2$PN(benzyl)P(o-ethylphenyl)$_2$, (o-ethylphenyl)$_2$PN(1-cyclohexylethyl)P(o-ethylphenyl)$_2$, (o-ethylphenyl)$_2$PN(2-methylcyclohexyl)P(o-ethylphenyl)$_2$, (o-ethylphenyl)$_2$PN(cyclohexyl)P(o-ethylphenyl)$_2$, (o-ethylphenyl)$_2$PN(allyl)P(o-ethylphenyl)$_2$, (3-ethyl-2-thiophenyl)$_2$PN(methyl)P(3-ethyl-2-thiophenyl)$_2$, (2-ethyl-3-thiophenyl)$_2$PN(methyl)P(2-ethyl-3-thiophenyl)$_2$ and (2-ethyl-4-pyridyl)$_2$PN(methyl)P(2-ethyl-4-pyridyl)$_2$.

The process conditions may be selected such that the catalyst activity is more than 1 gram product per gram transition metal.

The process may be an $\alpha$-olefins trimerisation process.

The process may be an ethylene trimerisation process.

The process includes the step of combining, in any order, a heteroatomic ligand with a transition metal compound and an activator.

The process may include the step of generating a heteroatomic coordination complex in situ from a transition metal compound and a heteroatomic ligand. The process may include the step of adding a pre-formed coordination complex, prepared using a heteroatomic ligand and a transition metal compound, to a reaction mixture, or the step of adding separately to the reactor, a heteroatomic ligand and a transition metal compound such that a heteroatomic coordination complex of a transition metal is generated in situ. By generating a heteroatomic coordination complex in situ is meant that the complex is generated in the medium in which catalysis takes place. Typically, the heteroatomic coordination complex is generated in situ. Typically, the transition metal compound, and heteroatomic ligand are combined (both in situ and ex situ) to provide metal/ligand ratios from about 0.01:100 to 10 000:1, and preferably, from about 0.1:1 to 10:1.

The transition metal may be selected from chromium, molybdenum, tungsten, tantalum, vanadium and titanium. Preferably, the transition metal is chromium.

The transition metal compound which, upon mixing with the heteroatomic ligand and an activator, catalyses ethylene trimerisation in accordance with the invention, may be simple inorganic or organic salts, for example halides, acetylacetonoates, carboxylates, oxides, nitrates, sulfates and the like, as well as a co-ordination or organometallic complex, for example, chromium trichloride tris-tetrahydrofuran complex, (benzene)tricarbonyl chromium, chromium hexacarbonyl, molybdenum hexacarbonyl and the like. The preferred transition metal compounds are chromium (III) acetylacetonoate and chromium (III) 2-ethylhexanoate.

The heteroatomic ligand can be modified to be attached, for example, to a polymer chain so that the resulting heteroatomic coordination complex of the transition metal is soluble at elevated temperatures, but becomes insoluble at 25° C. This approach would enable the recovery of the complex from the reaction mixture for reuse and has been used for another catalyst as described by D. E. Bergbreiter et al., *J. Am. Chem. Soc.,* 1987, 109, 177-179. In a similar vein these transition metal complexes can also be immobilised by binding the heteroatomic ligands to silica, silica gel, polysiloxane or alumina backbone as, for example, demonstrated by C. Yuanyin et al., *Chinese J. React Pol.,* 1992, 1(2), 152-159 for immobilising platinum complexes.

The activator for use in the process may in principle be any compound that generates an active catalyst when combined with the heteroatomic ligand and the transition metal compound. Some systems may be self activating. Mixtures of activators may also be used. Suitable compounds include organoaluminium compounds, organoboron compounds, organic salts, such as methyllithium and methylmagnesium bromide, inorganic acids and salts, such as tetrafluoroboric acid etherate, silver tetrafluoroborate, sodium hexafluoroantimonate and the like.

Suitable organoaluminium compounds include compounds of the formula $AlR_3$, where each R is independently a $C_1$-$C_{12}$ alkyl, an oxygen containing moiety or a halide, and compounds such as $LiAlH_4$ and the like. Examples include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, and aluminoxanes. Aluminoxanes are well known in the art as typically oligomeric compounds which can be prepared by the controlled addition of water to an alkylaluminium compound, for example trimethylaluminium. Such compounds can be linear, cyclic, cages or mixtures thereof. Mixtures of different aluminoxanes may also be used in the process.

Examples of suitable organoboron compounds are boroxines, $NaBH_4$, triethylborane, tris(pentafluoropheny)borane, tributyl borate and the like.

The activator may also be or contain a compound that acts as a reducing or oxidising agent, such as sodium or zinc metal and the like, or oxygen and the like.

The activator may be selected from alkylaluminoxanes such as methylaluminoxane (MAO) and ethylaluminoxane (EAO) as well as modified alkylaluminoxanes such as modified methylaluminoxane (MMAO). Modified methylaluminoxane (a commercial product from Akzo Nobel) contains modifier groups such as isobutyl or n-octyl groups, in addition to methyl groups.

The transition metal compound and the aluminoxane, may be combined in proportions to provide Al/metal ratios from about 1:1 to 10 000:1, preferably from about 1:1 to 1000:1, and more preferably from 1:1 to 300:1.

The process may include the step of adding to the catalyst system a trialkylaluminium compound in amounts of between 0.01 to 100 mol per mol of alkylaluminoxane.

It should be noted that aluminoxanes generally also contain considerable quantities of the corresponding trialkylaluminium compounds used in their preparation. The presence of these trialkylaluminium compounds in aluminoxanes can be attributed to their incomplete hydrolysis with water. Any quantity of a trialkylaluminium compound quoted in this disclosure is additional to alkylaluminium compounds contained within the aluminoxanes.

The process may include the step of mixing the components of the catalyst system at any temperature between −20° C. and 250° C. in the presence of an olefin. The applicant has found that the presence of an olefin may stabilise the catalyst system.

The individual components of the catalyst system described herein may be combined simultaneously or sequentially in any order, and in the presence or absence of a solvent, in order to give an active catalyst. The mixing of the catalyst components can be conducted at any temperature between −20° C. and 250° C. The presence of an olefin during the mixing of the catalyst components generally provides a protective effect which may result in improved catalyst performance. The preferred temperature range may be between 20° C. and 100° C.

The catalyst system, in accordance with the invention, or its individual components, may also be immobilised by supporting it on a support material, for example, silica, alumina, $MgCl_2$, zirconia or mixtures thereof, or on a polymer, for example polyethylene, polypropylene, polystyrene, or poly (aminostyrene). The catalyst can be formed in situ in the presence of the support material, or the support can be pre-impregnated or premixed, simultaneously or sequentially, with one or more of the catalyst components. In some cases, the support material can also act as or as a component of the activator. This approach would also facilitate the recovery of the catalyst from the reaction mixture for reuse. The concept was successfully demonstrated with a chromium-based ethylene trimerisation catalyst by T. Monoi and Y. Sasaki, *J. Mol. Cat. A:Chem.,* 1987, 109, 177-179. In some cases, the support can also act as a catalyst component, for example where such supports contain aluminoxane functionalities or where the support is capable of performing similar chemical functions as an aluminoxane, which is for instance the case with IOLA™(a product from Grace Davison).

The reaction products, or in other words olefin oligomers, as described herein, may be prepared with the disclosed catalyst system by homogeneous liquid phase reaction in the presence or absence of an inert solvent, and/or by slurry reaction where the catalyst system is in a form that displays little or no solubility, and/or a two-phase liquid/liquid reaction, and/or a bulk phase reaction in which neat reagent and/or product olefins serve as the dominant medium, and/or gas phase reaction, using conventional equipment and contacting techniques.

The process may therefore also be carried out in an inert solvent. Any inert solvent that does not react with the activator can be used. These inert solvents may include any saturated aliphatic and unsaturated aliphatic as well as aromatic hydrocarbon and halogenated hydrocarbon. Typical solvents include, but are not limited to, benzene, toluene, xylene, cumene, heptane, cyclohexane, 1-hexene, ionic liquids and the like.

The process may be carried out at pressures from atmospheric to 500 barg. Ethylene pressures in the range of 10-100 barg are preferred. Particularly preferred pressures range from above 30-50 barg. Catalyst activities and/or selectivities improve with pressures above 1 barg.

The process may be carried out at temperatures from −20-250° C. Temperatures in the range of 0-120° C. are preferred. Particularly preferred temperatures range from 25-100° C.

Although the catalyst, its individual components, reagents, solvents and reaction products are generally employed on a once-through basis, any of these materials can, and are indeed preferred to, be recycled to some extent in order to minimise production costs.

The process may be carried out in a plant which includes any type of reactor. Examples of such reactors include, but are not limited to, batch reactors, semi-batch reactors and continuous reactors. The plant may include, in combination a) a reactor, b) at least one inlet line into this reactor for olefin reactant and the catalyst system, c) effluent lines from this reactor for oligomerisation reaction products, and d) at least one separator to separate the desired oligomerisation reaction products, wherein the catalyst system may include a heteroatomic coordination complex of a transition metal compound and an activator, as described herein.

In another embodiment of the process the reactor and a separator may be combined to facilitate the simultaneous formation of reaction products and separation of these compounds from the reactor. This process principle is commonly known as reactive distillation. When the catalyst system exhibits no solubility in the solvent or reaction products, and is fixed in the reactor so that it does not exit the reactor with the reactor product, solvent and unreacted olefin, the process principle is commonly known as catalytic distillation.

The trimerisation process described herein may be used in a process in which the trimerisation of ethylene and co-polymerisation occur simultaneously leading to the incorporation of the trimerisation products into a copolymer. One example of this type of process is described in U.S. Pat. No. 5,786,431.

According to a further aspect of the invention, there is provided a catalyst system, as described above, for the trimerisation of olefins. The catalyst system may include a heteroatomic ligand as described above and a transition metal compound. The catalyst system may also include an activator as described above.

The heteroatomic ligand may be described by the following general formula $(R)_nA\text{-}B\text{—}C(R)_m$ where A and C are independently selected from a group which comprises phosphorus, arsenic, antimony, oxygen, bismuth, sulphur, selenium, and nitrogen, and B is a linking group between A and C, and R is independently selected from any homo or hetero hydrocarbyl group and n and m is determined by the respective valence and oxidation state of A and C.

More specifically the ligand may be described by the following general formula: $(R^1)(R^2)A\text{-}B\text{-}C(R^3)(R^4)$, where A and C are independently phosphorus, arsenic, antimony, nitrogen and bismuth and B is a linking group between A and C. A and/or C may be a potential donor site for coordination with the transition metal.

A and/or C may be independently oxidised by S, Se, N or O.

A and C may be independently phosphorus or phosphorus oxidised by S or Se or N or O.

The heteroatomic ligand may be selected from a group of ligands having at least two heteroatoms, wherein each heteroatom contains hydrocarbyl, or heterohydrocarbyl groups without any electron donating substituents. The applicant believes that if the catalyst system contains a bidentate heteroatomic coordination complex with substituents on the ortho position of any aromatic group bound to A or C, it would lead to improvements in the selectivity of the catalyst system due to suppression of secondary trimerisation reactions. The applicant therefore believes that in most instances the absence of such electron donating substituents is beneficial in terms of the overall reaction selectivity towards 1-hexene.

B may be selected from any one of a group comprising: organic linking groups comprising a hydrocarbyl, substituted hydrocarbyl, heterohydrocarbyl and a substituted heterohydrocarbyl group; inorganic linking groups comprising single atom links; ionic links and a group comprising methylene, dimethylmethylene, 1,2-ethane, 1,2-phenylene, 1,2-propane, 1,2-catechol, 1,2-dimethylhydrazine, —B(phenyl)-, —Si$(CH_3)_2$—, —P(phenyl) and —N($R^5$)— where $R^5$ is hydrogen, a hydrocarbyl or substituted hydrocarbyl, a substituted heteroatom or a halogen. Preferably, B may be —N($R^5$)— and $R^5$ is a hydrocarbyl or a substituted hydrocarbyl group. $R^5$ may be hydrogen or may be selected from the groups consisting of alkyl, aryl, aryloxy, halogen, nitro, alkoxycarbonyl, carbonyloxy, alkoxy, aminocarbonyl, carbonylamino, dialkylamino, or derivatives thereof, and aryl substituted with any of these substituents.

Preferred $R^5$ groups include alkyl groups such as methyl.

B may exclude $(CH_2)_xY(CH_2)_y$, where Y is —P($R^6$)—, —N($R^6$)—, —As($R^6$)—, —Sb($R^6$)— or —S— and x and y are individually 1-15 and wherein $R^6$ is hydrogen or a halogen or a nitro group or a hydrocarbyl or a substituted hydrocarbyl group.

B may be selected to be a single atom spacer. A single atom linking spacer is defined as a substituted or non-substituted atom that is bound directly to A and C.

$R^1$, $R^2$, $R^3$ and $R^4$ are each independently hydrocarbyl, substituted hydrocarbyl, heterohydrocarbyl or substituted heterohydrocarbyl groups where any substituents are non-electron donating. The substituents may be non-polar groups. Preferably $R^1$, $R^2$, $R^3$ and $R^4$ may be substituted aromatic or substituted hetero-aromatic groups containing non-electron donating substituents on the atom adjacent to the atom bound to A or C. $R^1$, $R^2$, $R^3$ and $R^4$ may be substituted aromatic or substituted hetero-aromatic groups containing non-polar substituents on the atom adjacent to the atom bound to A or C.

Non-polar is defined by IUPAC as an entity without a permanent electric dipole moment.

Suitable non polar substituents may be a methyl, ethyl, propyl, propenyl, propynyl, butyl, isopropyl, isobutyl, t-butyl, pentyl, hexyl, cyclopentyl, 2-methylcyclohexyl, cyclohexyl, cylopentadienyl, phenyl, bi-phenyl, naphthyl, tolyl, xylyl, mesityl, ethenyl, and benzyl group, or the like.

Preferably two or more of $R^1$, $R^2$, $R^3$ and $R^4$ may be aromatic or heteroaromatic containing at least one non-electron donating substituent on the atom adjacent to the atom bound to A or C. More preferably $R^1$, $R^2$, $R^3$ and $R^4$ may be aromatic or hetero aromatic containing at least one non-polar substituent on the atom adjacent to the atom bound to A or C.

Suitable examples of $R^1$, $R^2$, $R^3$ and $R^4$ include, but are not limited to, methyl, ethyl, ethylenyl, propyl, propenyl, propynyl, butyl, cyclohexyl, 2-methylcyclohexyl, 2-ethylcyclohexyl, 2-isopropylcyclohexyl, benzyl, phenyl, tolyl, xylyl, o-methylphenyl, o-ethylphenyl, o-isopropylphenyl, o-t-butylphenyl, cumyl, mesityl, biphenyl, naphthyl, anthracenyl, methoxy, ethoxy, phenoxy, tolyloxy, dimethylamino, thiomethyl, thiophenyl, trimethylsilyl, dimethylhydrazyl and the like.

$R^1$, $R^2$, $R^3$ and $R^4$ may be independently aromatic or substituted aromatic groups where the substituent on the atom adjacent to the atom bound to A or C is non-electron donating. $R^1$, $R^2$, $R^3$ and $R^4$ may be independently aromatic or substituted aromatic groups where the substituent on the atom adjacent to the atom bound to A or C is not a polar group.

It is most preferred that all of $R^1$, $R^2$, $R^3$ and $R^4$ may be aromatic or hetero aromatic and each of $R^1$, $R^2$, $R^3$ and $R^4$ should be substituted on at least one of the atoms adjacent to the atom bound to A or C by a non-electron donating group. It is also preferred that $R^1$, $R^2$, $R^3$ and $R^4$ be aromatic or heteroaromatic and each of $R^1$, $R^2$, $R^3$ and $R^4$ be substituted on at least one of the atoms adjacent to the atom bound to A or C by a non-polar group.

Any of the groups $R^1$, $R^2$, $R^3$ and $R^4$ may independently be linked to one or more of each other or to the linking group B to form a cyclic structure together with A and C, A and B or B and C.

The ligand may also comprise multiple $(R)_n$A-B-C$(R)_m$ units. Not limiting examples of such ligands include dendrimeric ligands as well as ligands where the individual units are coupled either via one or more of the R groups or via the linking group B. More specific, but not limiting, examples of such ligands may include 1,2-di-(N(P(o-ethylphenyl)$_2$)$_2$)-benzene, 1,4-di-(N(P(o-ethylphenyl)$_2$)$_2$)-benzene, N($CH_2CH_2$N(P(o-ethylphenyl)$_2$)$_2$)$_3$ and 1,4-di-(P(o-ethylphenyl)N(methyl)P(o-ethylphenyl)$_2$)-benzene.

The ligands can be prepared using procedures known to one skilled in the art and procedures disclosed in published literature. Specific examples of these ligands are: (o-ethylphenyl)$_2$PN(methyl)P(o-ethylphenyl)$_2$, (o-isopropylphenyl)$_2$PN(methyl)P(o-isopropylphenyl)$_2$, (o-methylphenyl)$_2$PN(methyl)P(o-methylphenyl)$_2$, (o-ethylphenyl)$_2$PN(methyl)P(o-ethylphenyl)(phenyl), (o-ethylphenyl)$_2$PN(isopropyl)P(o-ethylphenyl)$_2$, (o-isopropyl)$_2$PN(isopropyl)P(o-isopropyl)$_2$, (o-methyl)$_2$PN(isopropyl)P(o-methyl)$_2$, (o-t-butylphenyl)$_2$PN(methyl)P(o-t-butylphenyl)$_2$, (o-t-butylphenyl)$_2$PN(isopropyl)P(o-t-butylphenyl)$_2$, (o-ethylphenyl)$_2$PN(pentyl)P(o-ethylphenyl)$_2$, (o-ethylphenyl)$_2$PN(phenyl)P(o-ethylphenyl)$_2$, (o-ethylphenyl)$_2$PN(p-methoxyphenyl)P(o-ethylphenyl)$_2$, (o-ethylphenyl)$_2$PN(benzyl)P(o-ethylphenyl)$_2$, (o-ethylphenyl)$_2$PN(1-cyclohexylethyl)P(o-ethylphenyl)$_2$, (o-ethylphenyl)$_2$PN(2-methylcyclohexyl)P(o-ethylphenyl)$_2$, (o-ethylphenyl)$_2$PN(cyclohexyl)P(o-ethylphenyl)$_2$, (o-ethylphenyl)$_2$PN(allyl)P(o-ethylphenyl)$_2$, (3-ethyl-2-thiophenyl)$_2$PN(methyl)P(3-ethyl-2-thiophenyl)$_2$, (2-ethyl-3-thiophenyl)$_2$PN(methyl)P(2-ethyl-3-thiophenyl)$_2$ and (2-ethyl-4-pyridyl)$_2$PN(methyl)P(2-ethyl-4-pyridyl)$_2$.

The catalyst system may have a catalyst activity of more than 1 gram product per gram transition metal.

The transition metal may be selected from chromium, molybdenum, tungsten, tantalum and titanium. Preferably, the transition metal is chromium.

The transition metal compound which, upon mixing with the heteroatomic ligand and an activator, catalyses ethylene trimerisation in accordance with the invention, may be a simple inorganic or organic salt, for example halides, acetylacetonoates, carboxylates, oxides, nitrates, sulfates and the like, as well as a co-ordination or organometallic complex, for example, chromium trichloride tris-tetrahydrofuran complex, (benzene)tricarbonyl chromium, chromium hexacarbonyl, molybdenum hexacarbonyl and the like. The preferred transition metal compounds are chromium (III) acetylacetonoate and chromium (III) 2-ethylhexanoate.

The activator may in principle be any compound that generates an active catalyst when combined with the heteroatomic ligand and the transition metal compound. Mixtures of activators may also be used. Suitable compounds include organoaluminium compounds, organoboron compounds, organic salts, such as methyllithium and methylmagnesium bromide, inorganic acids and salts, such as tetrafluoroboric acid etherate, silver tetrafluoroborate, sodium hexafluoroantimonate and the like.

The activator may be selected from alkylaluminoxanes such as methylaluminoxane (MAO) and ethylaluminoxane (EAO) as well as modified alkylaluminoxanes such as modified methylaluminoxane (MMAO). Modified methylaluminoxane (a commercial product from Akzo Nobel) contains modifier groups such as isobutyl or n-octyl groups, in addition to methyl groups.

The transition metal compound and the aluminoxane may be in such proportions relative to each other to provide Al/metal ratios from about 1:1 to 10 000:1, preferably from about 1:1 to 1000:1, and more preferably from 1:1 to 300:1.

The catalyst system may also include a trialkylaluminium compound in amounts of between 0.01 to 100 mol per mol aluminoxane.

According to a further aspect of the invention, there is provided a ligand, as described above, for a catalyst system, as described above, for the trimerisation of olefins.

The invention also extends to the identification and use of ligands suitable for use in a trimerisation of olefins process or catalyst system.

EXAMPLES OF PERFORMING THE INVENTION

The invention will now be described with reference to the following examples which are not in any way intended to limit the scope of the invention. The individual components of the examples may conceivably be omitted or substituted and, although not necessarily ideal, the invention may conceivably still be performed and these components are not to be taken as essential to the working of the invention.

In the examples that follow all procedures were carried out under inert conditions, using pre-dried reagents. Chemicals were obtained from Sigma-Aldrich or Strem Chemicals unless stated otherwise. All trialkylaluminium and aluminoxane compounds and solutions thereof were obtained from Crompton Gmbh, Akzo Nobel and Albemarle Corporation. In all the examples, the molar mass of methylaluminoxane (MAO) was taken to be 58.016 g/mol, corresponding to the ($CH_3$—Al—O) unit, in order to calculate the molar quantities of MAO used in the preparation of the catalysts described in the examples below. Similarly the molar mass of ethylaluminoxane (EAO) was taken as 72.042 g/mol, corresponding to the ($CH_3CH_2$—Al—O) building block, and that of modified methylaluminoxane prepared from a 70:30 mixture of trimethylaluminium and tri-isobutylaluminium as 70.7 g/mol corresponding to the ($Me_{0.70}$isonBu$_{0.30}$-Al—O) unit. Ethylene oligomerisation products were analysed by GC-MS and GC-FID.

The mixed heteroatomic PNP ligands were synthesised by reacting amines and phosphine chlorides $R_2PCl$ as described in (a) Ewart et al., *J. Chem. Soc.* 1964, 1543; (b) Dossett, S. J. et al, *Chem. Commun.,* 2001, 8, 699; (c) Balakrishna, M. S. et al, *J. Organomet. Chem.* 1990, 390, 2, 203). The respective phosphine chlorides $R_2PCl$ were prepared as described in literature (Casalnuovo, A. L. et al., *J. Am. Chem. Soc.* 1994, 116, 22, 9869; Rajanbabu, T. V. et al, *J. Org. Chem.* 1997, 62, 17, 6012).

Example 1

Preparation of the (o-Ethylphenyl)$_2$PN(Methyl)P(o-Ethylphenyl)$_2$ ligand

Example 1a

Preparation of o-ethylphenyl-magnesium bromide

Magnesium turnings (9.11 g, 0.375 mol) were treated with the 1-bromo-2-ethyl-benzene (10.37 ml, 0.075 mol) in THF (200 ml). A vigorous reaction ensued which was cooled in an ice bath. Once the reaction had dissipated, the reaction mixture was heated under reflux for 2 hours yielding the Grignard reagent.

Example 1b

Preparation of Bis(o-ethylphenyl) Phosphorus Chloride

The Grignard reagent was added dropwise over 2 hours with stirring to a solution of $PCl_3$ (2.62 ml, 0.03 mol) in THF (200 ml) at −78° C. After complete addition the dry ice/acetone bath was removed and the reaction was allowed to warm to room temperature. The reaction was left stirring overnight and the solvent removed in vacuo. The crude product was found to be a mixture of (Br:Cl)-phosphines. This crude product was not isolated and all was used in the next step

Example 1c

Preparation of (o-Ethylphenyl)$_2$PN(methyl)P(o-Ethylphenyl)$_2$

The Bis(o-ethylphenyl) phosphorus chloride (30 mmol from the crude reaction mixture) was added to a solution of methylamine (2.0 M sol. in THF, 6.5 ml, 13.0 mmol) in DCM (80 ml) and triethylamine (15 ml) at 0° C. The reaction was stirred for 30 min after which the ice bath was removed. After stirring for a total of 14 hrs the solution was filtered to remove the triethylammonium salt formed. The product was isolated after crystallisation in 85% yield. $^{31}P\ \{H\}$ NMR: 57.45 ppm (s)

Example 2

Ethylene Trimerisation Reaction Using $CrCl_3$.(Tetrahydrofuran)$_3$, (o-ethylphenyl)$_2$PN(methyl)P(o-ethylphenyl)$_2$, and MAO A solution of 33.7 mg of (o-ethylphenyl)$_2$PN(methyl)P(o-ethylphenyl)$_2$ (0.066 mmol) in 5 ml of toluene was added to a solution of 12.4 mg $CrCl_3$.(Tetrahydrofuran)$_3$ (0.033 mmol) in 15 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 35° C. The pressure reactor was charged with ethylene after which the reactor temperature was maintained at 45° C., while the ethylene pressure was allowed to gradually increase to 45 barg over a period of 15 minutes. Thorough mixing was ensured throughout by mixing speeds of 1100 RPM's using a gas entraining stirrer. The reaction was terminated after 15 minutes by discontinuing the ethylene feed to the reactor and cooling the reactor to below 20° C. After releasing the excess ethylene from the autoclave, the reaction mixture in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid wax polymeric products. These solid products were dried overnight in an oven at 100° C. and then weighed to yield 0.4358 g of polyethylene. The GC analyses indicated that the reaction mixture contained 68.91 g oligomers. The product distribution of this example is summarised in Table 1.

Example 3

Ethylene Trimerisation Reaction using $CrCl_3$.(Tetrahydrofuran)$_3$, (o-ethylphenyl)$_2$PN(methyl)P(o-ethylphenyl)$_2$ and MAO A solution of 22.5 mg of (o-ethylphenyl)$_2$PN(methyl)P(o-ethylphenyl)$_2$ (0.044 mmol) in 5 ml of toluene was added to a solution of 8.3 mg $CrCl_3$.(Tetrahydrofuran)$_3$ (0.022 mmol) in 15 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 6.6 mmol) at 35° C. The pressure reactor was charged with ethylene after which the reactor temperature was maintained at 45° C., while the ethylene pressure was kept at 45 barg. Thorough mixing was ensured throughout by mixing speeds of 1100 RPM's using a gas entraining stirrer. The reaction was terminated after 30 minutes by discontinuing the ethylene feed to the reactor and cooling the reactor to below 20° C. After releasing the excess ethylene from the autoclave, the reaction mixture in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid polymeric products. These solid products were dried overnight in an oven at 100° C. and then weighed to yield 0.5033 g of polyethylene. The GC analyses indicated that the reaction mixture contained 102.60 g oligomers. The product distribution of this example is summarised in Table 1.

Example 4

Ethylene Trimerisation Reaction Using Cr(III) acetylacetonoate, (o-ethylphenyl)$_2$PN(methyl)P(o-ethylphenyl)$_2$ and MAO A solution of 33.7 mg of (o-ethylphenyl)$_2$PN(methyl)P(o-ethylphenyl)$_2$ (0.066 mmol) in 5 ml of toluene was added to a solution of 11.5 mg Cr(III) acetylacetonoate (0.033 mmol) in 15 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 45° C. The pressure reactor was charged with ethylene after which the reactor temperature was maintained at 55° C., while the ethylene pressure was kept at 45 barg. Thorough mixing was ensured throughout by mixing speeds of 1100 RPM's using a gas entraining stirrer. The reaction was terminated after 10 minutes by discontinuing the ethylene feed to the reactor and cooling the reactor to below 20° C. After releasing the excess ethylene from the autoclave, the reaction mixture in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid polymeric products. These solid products were dried overnight in an oven at 100° C. and then weighed to yield 0.3665 g of polyethylene. The GC analyses indicated that the reaction mixture contained 41.72 g oligomers. The product distribution of this example is summarised in Table 1.

Example 5

Ethylene Trimerisation Reaction Using Cr(III) acetylacetonoate, (o-ethylphenyl)$_2$PN(methyl)P(o-ethylphenyl)$_2$ and MAO A solution of 33.7 mg of (o-ethylphenyl)$_2$PN(methyl)P(o-ethylphenyl)$_2$ (0.066 mmol) in 5 ml of toluene was added to a solution of 11.5 mg Cr(III) acetylacetonoate (0.033 mmol) in 15 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 4.95 mmol) at 45° C. The pressure reactor was charged with ethylene after which the reactor temperature was maintained at 45° C., while the ethylene pressure was kept at 45 barg. Thorough mixing was ensured throughout by mixing speeds of 1100 RPM's using a gas entraining stirrer. The reaction was terminated after 10 minutes by discontinuing the ethylene feed to the reactor and cooling the reactor to below 20° C. After releasing the excess ethylene from the autoclave, the reaction mixture in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid polymeric products. These solid products were dried overnight in an oven at 100° C. and then weighed to yield 2.03 g of polyethylene. The GC analyses indicated that the reaction mixture contained 15.63 g oligomers. The product distribution of this example is summarised in Table 1.

Example 6

Ethylene Trimerisation Reaction Using Cr(III) acetylacetonoate, (o-ethylphenyl)$_2$PN(methyl)P(o-ethylphenyl)$_2$ and MAO A solution of 11.1 mg of (o-ethylphenyl)$_2$PN(methyl)P(o-ethylphenyl)$_2$ (0.022 mmol) in 5 ml of toluene was added to a solution of 4 mg Cr(III) acetylacetonoate (0.012 mmol) in 15 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 3.3 mmol) at 45° C. The pressure reactor was charged with ethylene after which the reactor temperature was maintained at 45° C., while the ethylene pressure was kept at 45 barg. Thorough mixing was ensured throughout by mixing speeds of 1100 RPM's using a gas entraining stirrer. The reaction was terminated after 10 minutes by discontinuing the ethylene feed to the reactor and cooling the reactor to below 20° C. After releasing the excess ethylene from the autoclave, the reaction mixture in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid polymeric products. These solid products were dried overnight in an oven at 100° C. and then weighed to yield 1.1 g of polyethylene. The GC analyses indicated that the reaction mixture contained 32.16 g oligomers. The product distribution of this example is summarised in Table 1.

Example 7

Ethylene Trimerisation Reaction Using Cr(III) (2-ethylhexanoate), (o-ethylphenyl)$_2$PN(methyl)P(o-ethylphenyl)$_2$ and MAO A solution of 33.7 mg of (o-ethylphenyl)$_2$PN(methyl)P(o-ethylphenyl)$_2$ (0.066 mmol) in 5 ml of toluene was added to a solution of 22.7 mg Cr(III) (2-ethylhexanoate) (70 mass % in mineral oil, 0.033 mmol) in 15 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 35° C. The pressure reactor was charged with ethylene after which the reactor temperature was maintained at 55° C., while the ethylene pressure was kept at 45 barg. Thorough mixing was ensured throughout by mixing speeds of 1100 RPM's using a gas entraining stirrer. The reaction was terminated after 10 minutes by discontinuing the ethylene feed to the reactor and cooling the reactor to below 20° C. After releasing the excess ethylene from the autoclave, the reaction mixture in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid polymeric products. These solid products were dried overnight in an oven at 100° C. and then weighed to yield 0.8270 g of polyethylene. The GC analyses indicated that the reaction mixture contained 86.57 g oligomers. The product distribution of this example is summarised in Table 1.

Example 8

Ethylene Trimerisation Reaction Using Cr(III) (2-ethylhexanoate), (o-methylphenyl)$_2$PN(methyl)P (o-methylphenyl)$_2$ and MAO A solution of 30.1 mg of (o-methylphenyl)$_2$PN(methyl)P (o-methylphenyl)$_2$ (0.066 mmol) in 5 ml of toluene was added to a solution of 22.7 mg Cr(III) (2-ethylhexanoate) (70 mass % in mineral oil, 0.033 mmol) in 15 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 55° C. The pressure reactor was charged with ethylene after which the reactor temperature was maintained at 60° C., while the ethylene pressure was kept at 45 barg. Thorough mixing was ensured throughout by mixing speeds of 1100 RPM's using a gas entraining stirrer. The reaction was terminated after 10 minutes by discontinuing the ethylene feed to the reactor and cooling the reactor to below 20° C. After releasing the excess ethylene from the autoclave, the reaction mixture in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid polymeric products. These solid products were dried overnight in an oven at 100° C. and then weighed to yield 0.5009 g of polyethylene. The GC analyses indicated that the reaction mixture contained 70.18 g oligomers. The product distribution of this example is summarised in Table 1.

Example 9

Ethylene Trimerisation Reaction Using Cr(III) acetylacetonoate, (o-methylphenyl)$_2$PN(Me)P(o-methylphenyl)$_2$ and MAO A solution of 30.1 mg of (o-methylphenyl)$_2$PN(Me)P(o-methylphenyl)$_2$ (0.066 mmol) in 5 ml of toluene was added to a solution of 11.5 mg Cr(III) acetylacetonoate (0.033 mmol) in 15 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 45° C. The pressure reactor was charged with ethylene after which the reactor temperature was maintained at 45° C., while the ethylene pressure was kept at 45 barg. Thorough mixing was ensured throughout by mixing speeds of 1100 RPM's using a gas entraining stirrer. The reaction was terminated after 13 minutes by discontinuing the ethylene feed to the reactor and cooling the reactor to below 20° C. After releasing the excess ethylene from the autoclave, the reaction mixture in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid polymeric products. These solid products were dried overnight in an oven at 100° C. and then weighed to yield 0.9579 g of polyethylene. The GC analyses indicated that the reaction mixture contained 70.89 g oligomers. The product distribution of this example is summarised in Table 1.

Example 10

Ethylene Trimerisation Reaction Using Cr(III) acetylacetonoate, (o-isopropylphenyl)$_2$PN(methyl)P(o-isopropylphenyl)$_2$ and MAO A solution of 37.5 mg of (o-isopropylphenyl)$_2$PN(Me)P(o-isopropylphenyl)$_2$ (0.066 mmol) in 5 ml of toluene was added to a solution of 11.5 mg Cr(III) acetylacetonoate (0.033 mmol) in 15 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 45° C. The pressure reactor was charged with ethylene after which the reactor temperature was maintained at 45° C., while the ethylene pressure was kept at 45 barg. Thorough mixing was ensured throughout by mixing speeds of 1100 RPM's using a gas entraining stirrer. The reaction was terminated after 13 minutes by discontinuing the ethylene feed to the reactor and cooling the reactor to below 20° C. After releasing the excess ethylene from the autoclave, the reaction mixture in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid polymeric products. These solid products were dried overnight in an oven at 100° C. and then weighed to yield 1.3748 g of polyethylene. The GC analyses indicated that the reaction mixture contained 56.30 g oligomers. The product distribution of this example is summarised in Table 1.

Example 11

Ethylene Trimerisation Reaction Using Cr(III) acetylacetonoate, (o-ethylphenyl)$_2$PN(methyl)P(o-ethylphenyl)$_2$ and MMAO-3A A solution of 6.9 mg of (o-ethylphenyl)$_2$PN(methyl)P(o-ethylphenyl)$_2$ (0.0135 mmol) in 10 ml of toluene was added to a solution of 3.5 mg Cr(acac)$_3$ (0.01 mmol) in 10 ml toluene in a Schlenk vessel. The mixture was stirred for 5 min at ambient temperature and was then transferred to a 300 ml pressure reactor (autoclave) containing a mixture of toluene (77 ml) and MMAO-3A (modified methylaluminoxane, Akzo Nobel, 3.0 mmol) at 35° C. The pressure reactor was charged with ethylene after which the reactor temperature was maintained at 45° C., while the ethylene pressure was kept at 45 barg. Thorough mixing was ensured throughout by mixing speeds of 1100 RPM's using a gas entraining stirrer. The reaction was terminated after 30 minutes by discontinuing the ethylene feed to the reactor and cooling the reactor to below 20° C. After releasing the excess ethylene from the autoclave, the reaction mixture in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid polymeric products. These solid products were dried overnight in an oven at 100° C. and then weighed to yield 2.931 g of polyethylene. The GC analyses indicated that the reaction mixture contained 48.29 g oligomers. The product distribution of this example is summarised in Table 1.

Example 12

Ethylene Trimerisation Reaction Using Cr(III) acetylacetonoate, (o-ethylphenyl)$_2$PN(methyl)P(o-ethylphenyl)$_2$ and EAO/TMA A solution of 33.7 mg of (o-ethylphenyl)$_2$PN(methyl)P(o-ethylphenyl)$_2$ (0.066 mmol) in 10 ml of toluene was added to a solution of 11.5 mg Cr(acac)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml), EAO (ethylaluminoxane, 33 mmol) and TMA (trimethylaluminium, 0.80 ml, 8.3 mmol) at 40° C. The pressure reactor was charged with ethylene after which the reactor temperature was maintained at 45° C., while the ethylene pressure was kept at 45 barg. Thorough mixing was ensured throughout by mixing speeds of 1100 RPM's using a gas entraining stirrer. The reaction was terminated after 46 minutes by discontinuing the ethylene feed to the reactor and cooling the reactor to below 20° C. After releasing the excess ethylene from the autoclave, the reaction mixture in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid polymeric products. These solid products were dried overnight in an oven at 100° C. and then weighed to yield 1.0 g of polyethylene. The GC analyses indicated that the reaction mixture contained 45.27 g oligomers. The product distribution of this example is summarised in Table 1.

Example 13

Ethylene Trimerisation Reaction Using Cr(octanoate)$_3$, (o-ethylphenyl)$_2$PN(methyl)P(o-ethylphenyl)$_2$ and MAO A solution of 16.0 mg of (o-ethylphenyl)$_2$PN(methyl)P(o-ethylphenyl)$_2$ (0.031 mmol) in 5 ml of toluene was added to a solution of 14.5 mg Cr(octanoate)$_3$, (0.021 mmol) in 15 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 4.0 mmol) at 35° C. The pressure reactor was charged with ethylene after which the reactor temperature was maintained at 45° C., while the ethylene pressure was kept at 45 barg. Thorough mixing was ensured throughout by mixing speeds of 1100 RPM's using a gas entraining stirrer. The reaction was terminated after 30 minutes by discontinuing the ethylene feed to the reactor and cooling the reactor to below 20° C. After releasing the excess ethylene from the autoclave, the reaction mixture in the autoclave was quenched with ethanol. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid polymeric products. These solid products were dried overnight in an oven at 100° C. and then weighed to yield 0.331 g of polyethylene. The GC analyses indicated that the reaction mixture contained 18.56 g oligomers. The product distribution of this example is summarised in Table 1.

Example 14

Ethylene Trimerisation Reaction Using Cr(III) acetylacetonoate, (o-ethylphenyl)$_2$PN(methyl)P(o-ethylphenyl)$_2$ and MAO in cyclohexane as Solvent A solution of 33.9 mg of (o-ethylphenyl)$_2$PN(methyl)P(o-ethylphenyl)$_2$ (0.066 mmol) in 5 ml of cyclohexane was added to a solution of 11.7 mg Cr(III) acetylacetonoate (0.033 mmol) in 15 ml cyclohexane in a Schlenk vessel. The mixture was stirred for 5 min at ambient temperature and was then transferred to a 300 ml pressure reactor (autoclave) containing a mixture of cyclohexane (71 ml) and MAO (methylaluminoxane, 9.9 mmol) in toluene (9 ml) at 45° C. The pressure reactor was charged with ethylene after which the reactor temperature was maintained at 45° C., while the ethylene pressure was kept at 45 barg. Thorough mixing was ensured throughout by mixing speeds of 1100 RPM's using a gas entraining stirrer. The reaction was terminated after 10 minutes by discontinuing the ethylene feed to the reactor and cooling the reactor to below 20° C. After releasing the excess ethylene from the autoclave, the reaction mixture in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid polymeric products. These solid products were dried overnight in an oven at 100° C. and then weighed to yield 3.2 g of polyethylene. The GC analyses indicated that the reaction mixture contained 37.53 g oligomers. The product distribution of this example is summarised in Table 1.

Example 15

Tandem Trimerisation and Co-Polymerisation Using $Cr(acac)_3$/(o-ethylphenyl)$_2$-PN(methyl)P(o-ethylphenyl)$_2$, cyclopentadienyl dimethylsilyl titanium dichloride and MAO In this example, 0,025 g of (o-ethylphenyl)$_2$-PN(methyl)P (o-ethylphenyl)$_2$ [0.06 mmol] was added to 10 ml of a toluene solution of $Cr(acac)_3$ [0.03 mmol] in a Schlenk tube under an argon atmosphere and allowed to stir for 5 minutes until fully dissolved. At the same time, 10 ml of a cyclopentadienyl dimethylsilyl titanium dichloride solution in toluene (0.03 mmol) was added to an external reservoir along with 10 ml anhydrous toluene. The external reservoir was connected to the inlet of an HPLC pump. After this, the 300 ml Parr autoclave was charged with 60 ml anhydrous toluene as well as the previously stirred $Cr(acac)_3$/(o-ethylphenyl)$_2$-PN(methyl)P (o-ethylphenyl)$_2$ ligand solution under inert conditions. Approximately 600 eq methylaluminoxane (MAO) was added to the autoclave under inert conditions. The autoclave was connected to the HPLC pump outlet and heated to 45° C., sealed and pressurized to 630 PSI with ethylene whilst stirring was commenced at 1200 rpm. At the same time the polymerization catalyst solution was added to the autoclave through the HPLC pump. The polymerization catalyst was added at a rate of 0.33 ml/min over a period of 60 minutes after which the reaction vessel was cooled down and quenched with ethanol. The autoclave was opened and the contents collected for analysis. The polymer collected was washed in acetone and dried in a vacuum oven for 12 h at 60° C. The dried polymer amounted to 12.5 g. Analysis of the polymer revealed two melting points at 96° C. (broad, onset at 114.92° C.) and one at 120.48° C. The total amount of 1-hexene incorporated was 7 mol % ($^{13}$C NMR).

TABLE 1

Ethylene trimerisation runs

| Example | Activity g prod./g Cr | Total Product g | Solids Wt % | Liquids Wt % | Liquid Product Distribution Wt % $C_4$ | $C_6$ | $C_8$ | $C_{10}$ | $C_{11+}$ | 1-Hexene in $C_6$ Wt % |
|---|---|---|---|---|---|---|---|---|---|---|
| 2 | 40415 | 69.35 | 0.63 | 99.37 | 0 | 93.6 | 3.7 | 2.7 | 0.1 | 99.8 |
| 3 | 89513 | 102.60 | 0.49 | 99.51 | 0 | 96.5 | 2.5 | 1.1 | 0 | 99.8 |
| 4 | 40977 | 42.08 | 0.87 | 99.13 | 0 | 94.2 | 4.2 | 1.3 | 0 | 99.7 |
| 5 | 10292 | 17.66 | 11.49 | 88.51 | 0 | 93 | 6.4 | 0.5 | 0 | 99.6 |
| 6 | 54018 | 32.16 | 3.42 | 96.58 | 0 | 94 | 4.4 | 1.6 | 0 | 99.7 |
| 7 | 50953 | 87.40 | 0.95 | 99.05 | 0.01 | 92.9 | 3.9 | 3.0 | 0.3 | 99.8 |
| 8 | 41120 | 70.70 | 0.71 | 99.29 | 0 | 85.3 | 11.8 | 2.3 | 0.6 | 99.3 |
| 9 | 46063 | 78.85 | 1.21 | 98.79 | 0 | 87.2 | 9.1 | 2.6 | 0 | 99.3 |
| 10 | 33614 | 57.68 | 2.38 | 97.62 | 0.1 | 95.2 | 2.8 | 0.7 | 0.3 | 99.3 |
| 11 | 98510 | 51.23 | 5.72 | 94.28 | 0.2 | 92.3 | 5.8 | 1.1 | 0.5 | 99.6 |
| 12 | 26964 | 46.27 | 2.16 | 97.84 | 0.1 | 91.7 | 5.5 | 1.1 | 1.5 | 99.6 |
| 13 | 18166 | 18.89 | 1.75 | 98.25 | 0 | 92.6 | 6.8 | 0.4 | 0.1 | 99.5 |
| 14 | 21875 | 37.53 | 8.53 | 91.47 | 0 | 93.9 | 5.8 | 1.1 | 0 | 99.7 |

The invention claimed is:

1. A process for the trimerisation of olefins comprising contacting an olefinic feedstream with a catalyst system at a pressure above 100 kPa (1 barg), which catalyst system includes the combination of a chromium compound; and a heteroatomic ligand of the following general formula $$(R^1)(R^2)A\text{-}B\text{-}C(R^3)(R^4)$$

where

A and C are phosphorus;

B is a linking group between A and C and;

$R^1$, $R^2$, $R^3$ and $R^4$ are independently a hydrocarbyl group, a substituted hydrocarbyl group, a heterohydrocarbyl group or a substituted heterohydrocarbyl group and two or more of $R^1$, $R^2$, $R^3$ and $R^4$ are aromatic or heteroaromatic groups containing at least one non-polar substituent on the atom adjacent to the atom bound to A or C.

2. The process as claimed in claim 1, wherein ethylene is contacted with the catalyst system at a pressure of more than 10 barg.

3. The process as claimed in claim 1, wherein B is selected from the group consisting of an organic linking group containing a hydrocarbylene, a substituted hydrocarbylene, a heterohydrocarbylene and a substituted heterohydrocarbylene group; an inorganic linking group comprising a single atom linking spacer; and a group comprising methylene, dimethylmethylene, 1,2-ethylene, 1,2-phenylene, 1,2-propylene, 1,2-catecholate, $N(CH_3)$—N—$(CH_3)$—, —$B(R^5)$—, —$Si(R^5)_2$—, —$P(R^5)$— or —$N(R^5)$—, where $R^5$ is hydrogen, a hydrocarbyl or substituted hydrocarbyl, a substituted heteroatom or a halogen.

4. The process as claimed in claim 1, wherein B is a single atom linking spacer.

5. The process as claimed in claim 1, wherein B is —$N(R^5)$—, wherein $R^5$ is selected from the group consisting of hydrogen, alkyl, substituted alkyl, aryl, substituted aryl, aryloxy, substituted aryloxy, halogen, nitro, alkoxycarbonyl, carbonyloxy, alkoxy, aminocarbonyl, carbonylamino, dialkylamino, silyl groups or derivatives thereof, and an aryl group substituted with any of these substituents.

6. The process as claimed in claim 1, wherein $R^1$, $R^2$, $R^3$ and $R^4$ are independently selected from the group consisting of o-methylphenyl, o-ethylphenyl, o-isopropylphenyl, and o-t-butylphenyl, groups.

7. The process as claimed in claim 1 wherein the ligand is selected from the group consisting of (o-ethylphenyl)$_2$PN(methyl)P(o-ethylphenyl)$_2$,
(o-isopropylphenyl)$_2$PN(methyl)P(o-isopropylphenyl)$_2$,
(o-methylphenyl)$_2$PN(methyl)P(o-methylphenyl)$_2$,
(o-ethylphenyl)$_2$PN(methyl)P(o-ethylphenyl)(phenyl),
(o-ethylphenyl)$_2$PN(isopropyl)P(o-ethylphenyl)$_2$,
(o-isopropylphenyl)$_2$PN(isopropyl)P(o-isopropylpheyl)$_2$,
(o-methylphenyl)$_2$PN(isopropyl)P(o-methylphenyl)$_2$,
(o-t-butylphenyl)$_2$PN(methyl)P(o-t-butylphenyl)$_2$,
(o-t-butyl phenyl)$_2$PN(isopropyl)P(o-t-butylphenyl)$_2$,
(o-ethylphenyl)$_2$PN(pentyl)P(o-ethylphenyl)$_2$,
(o-ethylphenyl)$_2$PN(phenyl)P(o-ethylphenyl)$_2$,
(o-ethylphenyl)$_2$PN(p-methoxyphenyl)P(o-ethylpheflyl)$_2$,
(o-ethylphenyl)$_2$PN(benzyl)P(o-ethylpheflyl)$_2$,
(o-ethylphenyl)$_2$PN(1-cyclohexylethyl)P(o-ethylphenyl)$_2$,
(o-ethylphenyl)$_2$PN(2-methylcyclohexyl)P(o-ethylpheflyl)$_2$,
(o-ethylphenyl)$_2$PN(cyclohexyl)P(o-ethylpheflyl)$_2$,
(o-ethylphenyl)$_2$PN(allyl)P(o-ethylphenyl)$_2$,
(2-ethyl-3-thiopheneyl)$_2$PN (methyl)P(2-ethyl-3-thiopheneyl)$_2$, and
(2-ethyl-4-pyridyl)$_2$PN(methyl)P(2-ethyl-4-pyridyl)$_2$.

8. The process as claimed in claim 1, wherein the catalyst system is prepared by combining in any order the heteroatomic ligand with the chromium compound and an activator.

9. The process as claimed in claim 8, which includes the step of generating a heteroatomic coordination complex in situ from the chromium compound and the heteroatomic ligand.

10. The process as claimed in claim 1, which process includes the step of adding a pre-formed coordination complex, prepared using the heteroatomic ligand and the chromium compound, to a reaction mixture containing an activator.

11. The process as claimed in claim 8, wherein the chromium compound is selected from an inorganic or organic salt, a co-ordination or organometallic complex.

12. The process as claimed in claim 11, wherein the chromium compound is selected from the group consisting of chromium trichloride tris-tetrahydrofuran complex, (benzene)tricarbonyl chromium, chromium (III) octanoate, chromium (III) acetylacetonoate, chromium hexacarbonyl, and chromium (III) 2-ethylhexanoate.

13. The process as claimed in claim 12, wherein the chromium compound is selected from a complex selected from chromium (III) acetylacetonoate and chromium (III) 2-ethylhexanoate.

14. The process as claimed in claim 9, wherein the chromium compound and heteroatomic ligand are combined to provide a transition metal/ligand ratio from about 0.01:100 to 10 000:1.

15. The process as claimed in claim 14, wherein the chromium compound and heteroatomic ligand are combined to provide a transition metal/ligand ratio from about 0.1:1 to 10:1.

16. The process as claimed in claim 8, wherein the activator is selected from the group consisting of an organoaluminium compound, an organoboron compound, methyllithium, methylmagnesium bromide, tetrafluoroboric acid etherate, silver tetrafluoroborate and sodium hexafluoroantimonate.

17. The process as claimed in claim 16, wherein the activator is an alkylaluminoxane.

18. The process as claimed in claim 17, wherein the alkylaluminoxane, is selected from the group consisting of methylaluminoxane (MAO), ethylaluminoxane (EAO), modified alkylaluminoxanes (MMAO) and mixtures thereof.

19. The process as claimed in claim 17, wherein the chromium compound and the aluminoxane are combined in proportions to provide an Al/chromium ratio from about 1:1 to 10 000:1.

20. The process as claimed in claim 19, wherein the chromium compound and the aluminoxane are combined in proportions to provide an Al/chromium ratio from about 1:1 to 1000:1.

21. The process as claimed in claim 20, wherein the chromium compound and the aluminoxane are combined in proportions to provide an Al/chromium ratio from about 1:1 to 300:1.

22. The process as claimed in claim 17, which includes the step of adding to the catalyst system a trialkylaluminium compound in an amount of from 0.01 to 100 mol per mol of alkylaluminoxane.

23. The process as claimed in claim 1, which includes the step of mixing the components of the catalyst system at any temperature between −20° C. and 250° C. in the presence of an olefin.

24. The process as claimed in claim 23, wherein the temperature range is between 20° C. and 100° C.

25. The process as claimed in claim 1, wherein the process is carried out at temperatures in the range of 0-120° C.

26. The process as claimed in claim 1, wherein the process is carried out at a temperature range from 25-100° C.

27. The process as claimed in claim 1, which includes the step of adding a polymerisation catalyst so that co-polymerisation of the olefin and trimerisation product occurs simultaneously leading to the incorporation of the trimerisation products into a copolymer.

28. The process as claimed in claim 1, wherein the at least one non-polar substituent is selected from the group consisting of methyl, ethyl, propyl, propenyl, propynyl, butyl, isopropyl, isobutyl, t-butyl, pentyl, hexyl, cyclopentyl, 2-methylcyclohexyl, cyclohexyl, cyclopentadienyl, phenyl, bi-phenyl, naphthyl, tolyl, xylyl, mesityl, ethenyl, and benzyl.

* * * * *